United States Patent [19]

Cox

[11] Patent Number: 5,789,645
[45] Date of Patent: *Aug. 4, 1998

[54] ISOMERIZATION CATALYST AND PROCESS

[75] Inventor: William L. Cox, Houston, Tex.

[73] Assignee: Amoco Corporation, Chicago, Ill.

[*] Notice: The term of this patent shall not extend beyond the expiration date of Pat. No. 5,545,792.

[21] Appl. No.: 669,514

[22] PCT Filed: Nov. 20, 1995

[86] PCT No.: PCT/US95/15223

§ 371 Date: Oct. 10, 1996

§ 102(e) Date: Oct. 10, 1996

[87] PCT Pub. No.: WO96/16006

PCT Pub. Date: May 30, 1996

[51] Int. Cl.⁶ .................. C07C 5/25; B01J 31/14
[52] U.S. Cl. .................. 585/665; 585/670; 502/170; 502/152
[58] Field of Search ................. 502/170, 152, 502/332, 154; 585/664, 665, 670

[56] References Cited

U.S. PATENT DOCUMENTS

| | | | |
|---|---|---|---|
| Re. 32,533 | 10/1987 | Trepka et al. | 44/62 |
| 3,409,681 | 11/1968 | Kroll | 260/666 |
| 3,412,174 | 11/1968 | Kroll | 260/683.9 |
| 4,493,919 | 1/1985 | Durbin et al. | 524/505 |
| 5,545,792 | 8/1996 | Cox | 585/665 |

FOREIGN PATENT DOCUMENTS 1329140  9/1973  United Kingdom.

*Primary Examiner*—Glenn Caldarola
*Assistant Examiner*—Thuan D. Dang
*Attorney, Agent, or Firm*—James R. Henes; Stephen L. Hensley

[57] ABSTRACT

A catalyst composition effective for isomerizing alpha-olefin to internal olefin and a process for conducting such isomerization using the catalyst composition are described. The catalyst comprises the combination of an alkyl aluminum alkoxide and a cobalt salt of an organic carboxylic acid or reduced form of such cobalt salt wherein the number of alkoxide groups in the alkyl aluminum alkoxide is sufficiently greater than 1 and sufficiently less than 3 per aluminum atom to provide an active catalyst for catalyzing such isomerization. Typically the alkyl aluminum alkoxide has the formula $R^3{}_n Al(OR^4)_p$ where $R^3$ and $R^4$ are the same or different and are alkyl, n is from 0.75 to 1.85, p is from 1.15 to 2.25 and the sum of n and p is 3. The isomerization process using such catalysts proceeds rapidly and requires no addition of hydrogen to enhance the reaction. Failure to achieve the proper balance between alkoxide and alkyl groups on the alkyl aluminum alkoxide results in an inactive catalyst or a catalyst that is only minimally effective even at high temperatures.

23 Claims, No Drawings

ISOMERIZATION CATALYST AND PROCESS

FIELD OF THE INVENTION

This invention relates to a catalyst mixture and the use of such catalyst mixture in the isomerization of alpha-olefins. More particularly, this invention relates to a novel catalyst mixture prepared by admixing an alkyl aluminum alkoxide and a cobalt salt of an organic carboxylic acid.

BACKGROUND OF THE INVENTION

Organoaluminum compounds have been previously utilized in the preparation of catalysts such as Ziegler-type catalysts. These catalysts preparations are based on the ability of organoaluminum compounds to act as reducing agents, i.e., reducing a transition metal to the zero valence state, e.g., U.S. Pat. No. 3,113,986.

U.S. Pat. No. 2,959,607 discloses the preparation of aluminum alkyls which contain at least one n-octyl group by subjecting octene-2 to the action of at least a stoichiometric amount of triisobutyl aluminum in the presence of a cobalt chloride catalyst at substantially atmospheric pressure. The catalyst apparently acts as both an isomerization and displacement catalyst in this process. The aluminum alkyls can be oxidized and hydrolyzed to make octanol-1.

U.S. Pat. No. 2,962,513 discloses a process for forming longer chain aluminum alkyls by a catalyzed olefin displacement of ethylene from ethyl aluminum compounds using a 100 to 300 percent stoichiometric excess of $C_3$ or higher alpha-olefins. The process uses salts and oxides of Group VIII metal as catalysts at temperatures of from about 50° to 200° C. at atmospheric pressure. Ethylene is evolved in the reaction.

U.S. Pat. No. 3,784,623 discloses the control of the increased tendency of the alpha-olefins to isomerize to internal olefins, which tendency is associated with catalytic displacement, by adding inhibitors or catalyst inactivators to the process.

U.S. Pat. No. 3,439,054 discloses a carbonyl catalyst that is useful for both hydrogenation of various unsaturated compounds as well as for causing isomerization in such compounds. The catalyst is dissolved as a mixture of transition metal carbonyl and an organoaluminum compound. This patent notes that organoaluminum compounds, such as alkoxides or halides, do not produce an active catalyst when used with the transition metal complex disclosed therein.

U.S. Pat. No. 3,409,681 discloses a solid Ziegler-type catalyst system for use in hydrogenation, dehydrogenation, isomerization, and hydrogen transfer reactions. The catalyst is formed from a transition metal compound in which the metal is selected from Groups I-B to VIII-B of the Periodic Table reduced by trimethylaluminum, dimethylmagnesium, or compounds of the formula $Al(CH_3)_2Y$ wherein Y is halogen, hydrogen, pseudo halogen (such as a CN group), lower alkoxide (such as methoxide and ethoxide) or azide. The use of such methyl-substituted organometallic reducing agents is described as critical for producing a solid catalyst system that can be used in heterogeneous liquid and gas phase reaction systems.

BRIEF SUMMARY OF THE INVENTION

This invention provides a novel catalyst system especially useful for isomerization of alpha-olefins to internal olefins. The catalyst enables such isomerization to proceed at high reaction rates and thereby substantially improve reactor throughput. Also the components used in forming the catalyst are typically proportioned such that if any solids are formed, they are colloidal solids whereby the catalyst behaves as a homogeneous catalyst, i.e., as if fully in solution.

More particularly, it has been found that the combination of an alkyl aluminum alkoxide and a cobalt salt of an organic carboxylic acid or reduced form of such cobalt salt can form a novel, highly active catalyst for use in isomerization alpha-olefins to internal olefins provided that the alkyl aluminum alkoxide has more than 1 but no more than about 2.85 alkoxide groups per aluminum atom. On the other hand, if the alkyl aluminum alkoxide has only 1 alkoxide and 2 alkyl groups per aluminum atom, the combination of such dialkyl aluminum alkoxide with a cobalt salt of an organic carboxylic acid or reduced form of such cobalt salt is inactive or only minimally active as a catalyst for use in isomerization alpha-olefins to internal olefins. Thus this invention provides a catalyst composition effective for isomerizing alpha-olefin to internal olefin which comprises the combination of an alkyl aluminum alkoxide and a cobalt salt of an organic carboxylic acid or reduced form of such cobalt salt wherein the number of alkoxide groups in said alkyl aluminum alkoxide is sufficiently greater than 1 and sufficiently less than 3 (e.g., about 2.85 or less) per aluminum atom to provide an active catalyst for catalyzing such isomerization reaction. Catalysts of this invention having a brown coloration rather than a blue coloration constitute a preferred embodiment, especially when the catalyst composition is formed by a procedure similar to a titration procedure described hereinafter. Such brownish colored catalyst compositions constitute highly active forms of isomerization catalyst provided that the number of alkoxide groups per aluminum atom does not exceed about 2.85.

In accordance with another preferred embodiment of this invention, there is provided a catalyst that is a mixture of i) an alkyl aluminum alkoxide of the formula $R^3{}_nAl(OR^4)_p$, where $R^3$ and $R^4$ are alkyl and n is from 0.75 to 1.85, p is from 1.15 to 2.25 and the sum of n and p is 3, and ii) a cobalt salt of an organic carboxylic acid or reduced form thereof.

In a further embodiment the catalyst is used in a process for preparing internal olefins of the formula

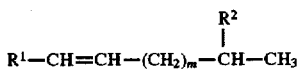

where $R^1$ is an alkyl group and $R^2$ is either a hydrogen atom or an alkyl group and m is an integer from 0 to 20 from alpha-olefins of the formula

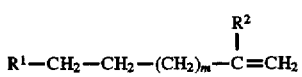

where $R^1$, $R^2$ and m are as previously defined.

The internal olefins are useful when oligomerized as oils. Depending on their viscosity, different applications for such oils are known, e.g., as lubricants. These materials are mixtures of different percentages of dimer, trimer, tetramer, pentamer and higher oligomers which oligomers are produced in different proportions in the oligomerization process. In order to increase the viscosity, processes are used which either produce more of the higher oligomers or some of the lower oligomers are removed such as by distillation. Most low viscosity dimer and trimer products are obtained as by-products of the production of higher viscosity synthetic oils. Due to the increasing use of dimers in applications such as low temperature lubricants and drilling fluids, methods for their preferential production are of interest.

DETAILED DESCRIPTION

The olefins used in making the internal olefin are predominately (at least 50 mole percent) $C_6$ to $C_{20}$ straight- or branched-chain monoolefinically unsaturated hydrocarbons in which the olefinic unsaturation occurs at the 1- or alpha-position of the carbon chain. Typically they have the following formula

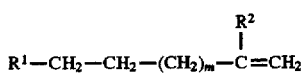

$$R^1-CH_2-CH_2-(CH_2)_m-\underset{\underset{R^2}{|}}{C}=CH_2$$

where $R^1$ and $R^2$ are the same or different and hydrogen or are alkyl, i.e. $C_1$ to $C_{20}$ linear or branched alkyl, preferably $C_1$ to $C_6$ linear or branched alkyl, most preferably $C_1$ to $C_4$ linear or branched alkyl, e.g. methyl, ethyl and the like, and m is an integer from 0 to 20. Particularly preferred are components where $R_1$ is alkyl and $R^2$ is hydrogen.

Such alpha-olefins are commercially available and can be made by the thermal cracking of paraffinic hydrocarbons or by the well-known Ziegler ethylene chain growth and displacement on triethyl aluminum. Individual olefins may be used as well as mixtures of such olefins. Examples of such olefins are 1-hexene, 1-heptene, 1-octene, 1-nonene, 1-decene, 1-dodecene, 1-tetradecene and 1-hexadecene. The more preferred normal-alpha-olefin monomers are those containing about 8–12 carbon atoms. The most preferred olefin monomer is 1-decene.

The alpha-olefins can also contain minor amounts of up to about 50 and usually less than 25 mole percent of internal olefins and vinylidene olefins. Typically above 70% of the olefins is 1-decene.

The alpha-olefin or mixture of alpha-olefins is contacted with a catalytically effective amount of a catalyst mixture comprising an alkyl aluminum alkoxide as described above and a cobalt (II) salt of an organic carboxylic acid or a reduced form thereof.

The alkyl aluminum alkoxide portion of the catalyst has the formula $R^3{}_nAl(OR^4)_p$ where $R^3$ and $R^4$ are alkyl as defined above and n is from 0.75 to 1.85 (preferably from 0.75 to 1.75), p is from 1.15 to 2.25 (preferably from 1.25 to 2.25) and the sum of n and p is 3. Most preferably n is 1 or very close to 1 (e.g., 0.95 to 1.05) and p is 2 or very close to 2 (e.g., 1.95 to 2.05). The alkyl aluminum alkoxide can be a single compound (i.e., an alkyl aluminum dialkoxide), but in most cases it is a mixture of $R^3Al(OR^4)_2$ and $(R^3)_2AlOR^4$ proportioned such that the overall product has n alkyl groups and p alkoxide groups where n and p are as defined above and the sum of n and p is 3. From the cost effectiveness standpoint $R^3$ and $R^4$ each have at least two carbon atoms, as such alkyl groups can be, and usually are, derived from olefins. In addition, alkyl aluminum alkoxides with two or more carbon atoms in each alkyl group are highly compatible with, and have good solubility in, olefin isomerization reaction mixtures.

The alkyl aluminum alkoxide can be formed by processes well known to those skilled in the art, i.e., by controlled oxidation of aluminum alkyl. However in preferred embodiments of this invention the alkyl aluminum alkoxide in formed by addition to the reactor of suitable proportions of aluminum trialkyl and cobalt carboxylate (e.g., a cobalt dicarboxylate or tricarboxylate such as cobaltous or cobaltic acetate, and other cobalt salts such as the hexanoates, octanoates, decanoates, and the like, whereby the alkyl aluminum alkoxide is generated in situ presumably by oxygen atoms released from the cobalt carboxylate as it is reduced by the aluminum alkyl. Such in situ generation is preferred as it is much easier to produce alkyl aluminum alkoxides having the composition required for the practice of this invention (i.e., having the values for n and p given above). Thus in conducting the in situ formation of the alkyl aluminum alkoxide it is generally sufficient to calculate the quantities of aluminum trialkyl and cobalt salt based on the assumption that each carboxyl group of the cobalt carboxylate salt releases two oxygen atoms which convert two alkyl groups on the aluminum trialkyl to two alkoxide groups thereon. Thus when using a cobalt dicarboxylate the assumed stoichiometry is that each molecule of the cobalt salt yields 4 oxygen atoms. Since there are 3 alkyl groups on each molecule of aluminum trialkyl, use of two moles of aluminum trialkyl per mole of cobalt dicarboxylate results in a ratio of 1 alkyl group and 2 alkoxide groups on each aluminum atom which is a highly preferred ratio (i.e., in the above formula n is 1 and p is 2). Thus typically it is convenient to charge about 2 moles of aluminum trialkyl per mole of cobalt dicarboxylate. In practice some slight variance in the proportions of the aluminum trialkyl to cobalt carboxylate may be required to compensate for the purity level of the initial components and the inevitable presence of some free oxygen atoms even in an inert atmosphere. If using other forms of cobalt (e.g., a cobalt tricarboxylate or a cobalt complex or oxygen-containing chelate) the stoichiometry can readily be adjusted in accordance with the foregoing principles. Air oxidation, while workable, is much more difficult to control to form product with the above values for n and p. Moreover, air oxidation of aluminum trialkyls tends to produce aluminum metal or other solids which can cause pluggage or other operational problems.

The catalyst mixture in accordance with the present invention, in addition to the alkyl aluminum alkoxide preferably utilizes as the cocatalyst component a cobalt (II) salt. Suitable cobalt salts include, but are not intended to be limited to complexes such as cobalt acetylacetonate, and preferably, the organic carboxylic acid salts such as the cobalt (II) carboxylates, i.e., cobalt naphthenate, cobalt acetate, cobalt tallate, cobalt stearate, cobalt 2-ethylhexanoate, and the like. The salts are preferably anhydrous salts.

The amount of cobalt salt used as the cocatalyst is relatively small in comparison to the amount of alkyl aluminum alkoxide. In all cases the atom ratio of cobalt to aluminum is less than 1:1, typically and preferably in the vicinity of about 0.5 to 1 or less. Experiments have indicated that a particularly preferred ratio of cobalt to aluminum is from 0.05 to 0.2 when the alkyl aluminum alkoxide is formed in situ by reaction of an aluminum trialkyl with the oxygen atoms liberated from cobalt dicarboxylate used therewith in forming the catalyst. Based on the alpha-olefin, the amount of cobalt salt charged is about 0.001 to about 0.10%, preferably about 0.001 to about 0.005%, most preferably about 0.001 to about 0.003% on a weight basis.

It is to be understood and appreciated that the precise composition of the reduced form of the initial cobalt carboxylic acid salt is not known. Thus it may or may not contain residual carboxyl or carboxylate groups. Because both aluminum trialkyls and alkyl aluminum alkoxides are reducing agents, it is possible that even where fresh cobalt carboxylate is added to a preformed alkyl aluminum alkoxide to form a catalyst system of this invention, at least some reduction of the cobalt carboxylate may occur. Accordingly this invention is not intended to be limited to any particular structure or composition for the reduced form of the cobalt carboxylate. As long as the alkyl aluminum alkoxide satisfies the requirements for n and p as set forth above and is associated with either fresh cobalt carboxylate or the cobalt-containing residue resulting from in situ formation of the alkyl aluminum alkoxide to form an active olefin isomerization catalyst, the composition constitutes a catalyst of this invention. In this connection, no additional component beyond those specified herein that adversely affects the functioning of the catalyst in the isomerization processes of this invention is included in the catalyst systems of this invention.

The alkyl aluminum alkoxide, present with the alpha-olefin at the time of isomerization is (based on the amount of olefin) from about 0.1% to about 10% by weight. Catalyst concentrations higher than 10% may be used, if desired, but offer no particular advantage over lesser concentrations. For a typical isomerization reaction as contemplated by the present invention, alkoxide concentrations within the range of 0.5 to about 2.0% by weight of the vinyl olefins are preferred.

The isomerization reaction is conducted in a sealed substantially anhydrous vessel without air at a temperature that is not as low as to retard reaction but not too high such that catalyst activity is diminished due to catalyst decomposition. Thus temperatures in the range of 100° C. to 250° C. have been found conducive to the isomerization reaction, with a range of 150° C. to 200° C. being preferred and 160° C. to 180° C. being most preferred. The isomerization reaction can be conducted on a batch, continuous, or semi-continuous basis.

The i) cobalt (II) salt of an organic carboxylic acid, and ii) alkyl aluminum alkoxide admixture that is the catalyst of this invention is typically preformed and added to the reaction mixture as such or it may be formed in situ. Thus, for example, to a mixture of the cobalt (II) compound optionally in a suitable inert solvent, an alkyl aluminum alkoxide compound, optionally also in an inert solvent, may be added. The resulting mixture may then be added to the vinyl olefin to accomplish the present isomerization.

It is also possible, although definitely less preferable, to first add the alkyl aluminum alkoxide precursor, i.e., the trialkylaluminum to the olefin reaction mass having the cobalt (II) salt already present. After passing oxygen or air into this mass (by sparging for example) for a time suitable to convert the trialkylaluminum into the catalytically active alkyl aluminum alkoxide species (as described herein) the mixture is heated and isomerization effected. It should be noted that the cobalt (II) compound need not be present when such in situ oxidation is carried out but can be added prior to heating and isomerizing. As noted above, in situ formation of the catalyst is the preferred method of operation.

The catalyst systems of this invention are readily oxidized by the presence of oxygen, such as small amounts of air entrained in the olefin to be isomerized and/or in the inert gas under which the reaction should be conducted. Thus a catalyst system in which the alkyl aluminum alkoxide content satisfying the above values for n and p may become over-oxidized by the presence in the reaction system and/or in the olefin feed of such oxygen impurities. In such cases, the catalyst will attain a blue coloration indicating that the desired active catalyst complex from the alkyl aluminum alkoxide and cobalt carboxylate is no longer present in the system. Thus, under such conditions, little if any olefin isomerization will occur. To remedy this situation, small amounts of alkyl aluminum alkoxide or, more preferably, aluminum trialkyl should be added to the system until the color changes from a blue coloration to a brown coloration. At this point, the adverse effect of the oxygen impurities has been overcome through reduction of the over oxidized catalyst complex to the proper stage at which the catalyst system becomes highly active as an olefin isomerization catalyst. Therefore, in situations of this kind, a type of back titration of the catalyst mixture in the reaction system using color change (blue to brown) as the end point indicator is a desirable procedure to use for compensating for oxygen impurities present in the initial reaction system. When utilizing this back titration procedure, care should be taken not to add an excessive amount of the alkyl aluminum alkoxide or aluminum trialkyl as an excessive amount can push the composition of the catalyst beyond its proper makeup and thereby form a less active catalyst. Accordingly, in any given situation it may be found desirable with given materials used in the process to conduct a few pilot experiments utilizing the back titration procedure in order to standardize the quantities of the materials to be used in the isomerization process in order to achieve optimum performance under that given set of circumstances.

Another preferred embodiment of the invention is a process for isomerizing a mixture of olefins containing about 10–20 carbon atoms consisting mainly of vinyl olefins and vinylidene olefins and a minor amount of internal olefins. The process comprises heating the mixture of olefins in contact with a catalytic amount of a mixture of i) an alkyl aluminum alkoxide mixture of the compound of the formula $(R^3)_2Al(OR^4)$ and $R^3Al(OR^4)_2$, proportioned to provide the values for n and p as given above, and ii) a cobalt (II) salt of an organic carboxylic acid or reduced form thereof at a temperature of about 160° C. to 180° C. until a substantial amount of the vinyl olefins have isomerized to form isomerized internal olefins. The process is characterized in that the isomerized internal olefins formed from the vinyl olefins are mainly internal olefins containing 8–24 carbon atoms having the structure

X—CH=CH—Y and only a minor amount of tri-substituted internal olefins having the structure.

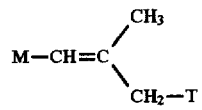

wherein X, Y, M and T are aliphatic hydrocarbon groups such that X plus Y contain about 6–22 carbon atoms and M plus T contain about 4–20 carbon atoms.

EXAMPLE 1

The following example illustrates vinyl olefin isomerization produced by the addition of aluminum alkoxide and a cobalt carboxylate:

1) A reaction apparatus is set up consisting of a 1000 mL creased flask, agitator, heating mantle, thermometer and nitrogen purge on the vapor space of the flask.
2) To the flask is added 500 g of olefins having the following analysis:

| G.C. Analysis | | NMR Analysis | |
|---|---|---|---|
| Component | Wt. % | Component | Mole % |
| $C_{14}$ Olefin | 0.81 | Vinyl | 58.69 |
| $C_{16}$ Olefin | 48.89 | Branched | 34.39 |
| $C_{18}$ Olefin | 41.64 | Internal | 6.92 |
| $C_{20}$ Olefin | 8.66 | Trisubstituted | 0.0 |

3) To the olefins is added 12.78 g of a mixed ($C_2$–$C_{20}$) aluminum alkoxide having a molar % oxidation of 60%.
4) The reactants are heated to 170° C. and 30 ppm cobalt is added in the form of cobalt 2-ethylhexanoate.
5) The reactants are maintained at 170° C. for 15 minutes and then cooled to room temperature.

6) The reaction product is next flashed distilled in a 5-tray Oldershaw column at 5 mm Hg vacuum to recover 471.5 g of catalyst free product having the following NMR analysis:

| NMR Analysis | |
|---|---|
| Component | Mole % |
| Vinyl | 1.7 |
| Branched | 20.6 |
| Internal | 68.2 |
| Trisubstituted | 9.4 |

EXAMPLE 2

The following example illustrates vinyl olefin isomerization produced by the addition of a cobalt carboxylate and an aluminum alkyl. The alkoxide is formed in situ by oxidation of the aluminum alkyl with the oxygen present in the cobalt salt.

1) A reaction apparatus is set up as described in Example 1.
2) To the reaction flask is added 500 g of olefins having the same composition as in Example 1.
3) The olefins are heated to 170° C. and 1.5 g of mixed ($C_2$–$C_{20}$) aluminum alkyls having an aluminum concentration of 7 wt. % are added.
4) To the reactants is added 40 ppm of cobalt in the form of cobalt 2-ethylhexanoate.
5) The reactants are maintained at 170° C. for 15 minutes and then cooled to room temperature.
6) The reaction product is then flash distilled as described in Example 1 to recover 432.2 g of catalyst free product having the following NMR analysis:

| NMR Analysis | |
|---|---|
| Component | Mole % |
| Vinyl | 1.1 |
| Branched | 15.0 |
| Internal | 68.7 |
| Trisubstituted | 15.2 |

EXAMPLE 3

The following example illustrates that vinyl olefin isomerization does not occur when a fully oxidized (98%) aluminum alkyl is used with cobalt catalyst.

1) A reaction apparatus is set up consisting of a 100 mL flask, agitator, heating mantle, thermometer and nitrogen purge on the vapor space of the flask.
2) To the flask is added 30 g of $C_{14}$ olefin having the following NMR analysis:

| NMR Analysis | |
|---|---|
| Component | Mole % |
| Vinyl | 80.51 |
| Branched | 14.57 |
| Internal | 4.92 |
| Trisubstituted | 0.0 |

3) To the olefin is added 0.50 g of a $C_8$ alkoxide having a molar % oxidation of 98%.
4) The reactants are heated to 175° C. and 30 ppm cobalt is added in the form of cobalt 2-ethylhexanoate.

5) The reactants are maintained at 180° C. for 15 minutes and then cooled to room temperature.
6) A 2 mL sample of the reaction product is hydrolyzed with 3 mL of 10% HCl to remove catalyst and a NMR analysis of the organic phase showed the composition to be identical with the starting olefin.

EXAMPLE 4

The following example illustrates that vinyl olefin isomerization with an excess of aluminum alkyl (very low oxidation level) produces a low conversion to internal olefin.

1) A reaction apparatus is set up as described in Example 3.
2) To the reaction flask is added 30 g of $C_{14}$ olefin having the same composition as in Example 3.
3) The olefin is heated to 170° C. and 0.452 g of mixed ($C_2$–$C_{20}$) aluminum alkyls having an aluminum concentration of 7 wt. % are added.
4) To the reactants is added 45 ppm of cobalt in the form of cobalt 2-ethylhexanoate.
5) The reactants are maintained at 170° C. for 30 minutes and then cooled to room temperature.
6) A 2 mL sample of the reaction product is hydrolyzed with 3 mL of 10% HCl to remove catalyst and a NMR of the organic phase gave the following:

| NMR Analysis | |
|---|---|
| Component | Mole % |
| Vinyl | 59.72 |
| Branched | 15.91 |
| Internal | 24.36 |
| Trisubstituted | 0.00 |

Only about 26% of the vinyl olefin was isomerized to internal olefins.

EXAMPLE 5

The following example illustrates the effect of the oxidation level of an aluminum trialkyl on isomerization rate of a $C_{14}$ alpha-olefin in an isomerization reaction conducted at about 200° C. The alkyl aluminum alkoxides are formed in situ by controlled oxidation of aluminum alkyl in a mixture to which cobalt carboxylate was added.

1) A reaction apparatus is set up as described in Example 1.
2) To the reaction flask are added 70 g of tri-n-octyl aluminum and 210 g of $C_{14}$ alpha-olefin.
3) The contents are heated to 71° C. and 10 ppm of cobalt is added as cobalt octanoate.
4) After 5 minutes the reaction mixture is cooled to 51°–55° C. and air feed is started to begin-partial oxidation of the aluminum trialkyl.
5) Samples (3 mL each) of the reaction mixture are taken in test tubes as the oxidation is proceeding, and each test tube with sample is immediately placed in an oil bath at 390° F. (ca 199° C.) for 2 minutes.
6) The heated samples are then quenched to room temperature and hydrolyzed with dilute hydrochloric acid.
7) The resulting samples are analyzed by GC to determine the percentage of oxidation of the initial aluminum trialkyl and the extent to which the $C_{14}$ olefin has been isomerized by the catalyst system at that oxidation stage.

The results of an experiment carried out in this manner are shown in the following table where Δ% Internal Olefin reflects the amount by which the internal olefin content of the reaction mixture had increased in 2 minutes at 390° F. in the presence of the catalyst system in which the extent of oxidation of alkyl groups on the original aluminum trialkyl to alkaxide groups was as shown:

| Sample | % Oxidation | % Internal Olefin | Δ % Internal Olefin |
|---|---|---|---|
| 2 | 6.6 | 17.2 | 7.5 |
| 4 | 23.2 | 20.2 | 9.8 |
| 5 | 34.2 | 27.2 | 16.3 |
| 6 | 46.7 | 35.5 | 24.1 |
| 7 | 58.4 | 44.6 | 32.7 |
| 7-1/2* | 63.0 | 36.3 | 24.1 |
| 8 | 71.0 | 20.45 | 7.5 |
| 9 | 86.0 | 16.65 | 0.5 |

*A mixture of samples 7 and 8

Another advantage of the process of this invention is that the isomerization can be conducted at high reaction rates without requiring addition of small amounts of hydrogen.

The most preferred catalysts of this invention are formed by adding aluminum trialkyl to a cobalt salt of an organic carboxylic acid in a substantially anhydrous liquid medium and under a substantially oxygen-free inert atmosphere, the addition being stopped at or shortly beyond the point at which the color of the mixture changes from a blue coloration to a brown coloration. This process and the catalysts prepared in this manner constitute additional preferred embodiments of this invention.

What is claimed is:

1. A process for producing an internal olefin of the formula

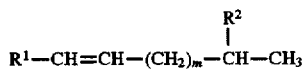

wherein $R^1$ is an alkyl group and $R^2$ is either a hydrogen atom or an alkyl group and m is an integer of from 0 to 20 comprising contacting a vinyl or vinylidene olefin of the formula

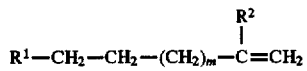

where $R^1$, $R^2$ and m are as previously defined, with a catalytically effective amount of a mixture of i) an aluminum compound of the formula $R^3{}_nAl(OR^4)_p$ where $R^3$ and $R^4$ are the same or different and are alkyl, n is of from 0.75 to 1.85, and p is from 1.15 to 2.25, the sum of n and p being 3, and ii) a cobalt salt of an organic carboxylic acid or reduced form thereof, at a temperature of from about 100° C. to about 250° C.

2. A process of claim 1 wherein $R^1$ is a substantially linear alkyl group and $R^2$ is a hydrogen atom.

3. A process of claim 1 wherein $R^1$ and $R^2$ are both alkyl groups such that the total number of carbon atoms in said vinylidene olefin is about 8–24.

4. A process of claim 1 wherein said temperature is about 150° C. to 200° C.

5. A process of claim 1 wherein the cobalt salt used in forming said mixture of i) and ii) is a cobalt (II) salt.

6. A process for isomerizing a mixture of olefins containing in the range of about 8–24 carbon atoms, said mixture of olefins consisting essentially of 50 to 95 weight percent of vinyl olefins and 5 to 50 weight percent of vinylidene olefins and a minor amount of internal olefins, said process comprising heating said mixture of olefins in contact with a catalytic amount of i) an aluminum compound of the formula $R^3{}_nAl(OR^4)_p$ wherein $R^3$ and $R^4$ are the same or different and are alkyl, n is from 0.75 to 1.75, and p is from 1.25 to 2.25, the sum of n and p being 3, and ii) a cobalt (II) salt of an organic carboxylic acid or reduced form thereof, at a temperature of about 160° C. to 180° C. until a substantial amount of said vinyl olefins have isomerized to form isomerized internal olefins, said process being characterized in that said isomerized internal olefins which are formed from said vinyl olefins are mainly internal olefins containing in the range of 8–24 carbon atoms and have the structure

X—CH=CH—Y and only a minor amount of tri-substituted internal olefins having the structure

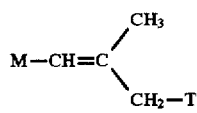

wherein X, Y, M and T are aliphatic hydrocarbon groups such that X plus Y contain in the range of about 6–22 carbon atoms and M plus T contain in the range of about 4–20 carbon atoms.

7. A process of claim 5 further characterized in that at least 70 weight percent of the vinyl olefins in said mixture of olefins is decene.

8. The process according to claim 1 or claim 6 wherein said aluminum compound and said reduced form of said salt are produced in situ by adding to said mixture of olefins an aluminum trialkyl and a cobalt carboxylate in proportions sufficient to provide an alkyl aluminum alkoxide in which n and p are as defined therein.

9. An isomerization catalyst composition composed of i) an alkyl aluminum alkoxide of the formula $R^3{}_nAl(OR^4)_p$ where R3 and R4 are the same or different and are alkyl, n is from 0.75 to 1.85, p is from 1.15 to 2.25 and the sum of n and p is 3, and ii) a cobalt carboxylate or reduced form thereof.

10. A catalyst according to claim 9 wherein n is from 0.75 to 1.75 and p is from 1.25 to 2.25 and wherein the sum of n and p is 3.

11. A catalyst according to claim 9 wherein n is from 0.95 to 1.05 and p is from 1.95 to 2.05 and wherein the sum of n and p is 3.

12. A catalyst according to any of claims 9, 10, or 11, wherein said cobalt carboxylate as initially introduced into the catalyst is a cobalt (II) carboxylate salt.

13. An isomerization catalyst composition comprising i) alkyl aluminum alkoxide of the formula $R^3{}_nAl(OR^4)_p$ where $R^3$ and $R^4$ are the same or different and are alkyl, n is in the range of from 0.75 to 1.85, p is in the range of from 1.15 to 2.25 and the sum of n and p is 3, and ii) a cobalt-containing residue, said catalyst formed by reacting aluminum trialkyl with cobalt carboxylate in relative proportions to yield said alkoxide while reducing said carboxylate, said proportions being calculated using as the basis for the calculation the assumption that each carboxylate group provides two oxygen atoms that convert two alkyl groups of the aluminum alkyl to two alkoxide groups per aluminum atom present.

14. A catalyst according to claim 13 wherein n is from 0.75 to 1.75 and p is from 1.25 to 2.25 and wherein the sum of n and p is 3.

15. A catalyst according to claim 13 wherein n is from 0.95 to 1.05 and p is from 1.95 to 2.05 and wherein the sum of n and p is 3.

16. A catalyst according to any of claims 13, 14, or 15, wherein said cobalt carboxylate as initially introduced into the catalyst is a cobalt (II) carboxylate salt.

17. A process of forming internal olefin which comprises isomerizing alpha-olefin to internal olefin in the presence of a catalyst of claim 9.

18. A process of forming internal olefin which comprises isomerizing alpha-olefin to internal olefin in the presence of a catalyst of claim 11.

19. A process of forming internal olefin which comprises isomerizing alpha-olefin to internal olefin in the presence of a catalyst of claim 13.

20. A process of forming internal olefin which comprises isomerizing alpha-olefin to internal olefin in the presence of a catalyst of claim 15.

21. A catalyst composition effective for isomerizing alpha-olefin to internal olefin which comprises the combination of an alkyl aluminum alkoxide and a cobalt salt of an organic carboxylic acid or reduced form of such cobalt salt wherein the number of alkoxide groups in said alkyl aluminum alkoxide is sufficiently greater than 1 and sufficiently less than 3 per aluminum atom to provide an active catalyst for catalyzing such isomerization.

22. A process of any individual claim of claims 17 through 20, wherein said cobalt carboxylate as initially introduced into the catalyst is a cobalt (II) carboxylate salt.

23. A catalyst composition of claim 22 characterized by having a brown coloration.

* * * * *

UNITED STATES PATENT AND TRADEMARK OFFICE
CERTIFICATE OF CORRECTION

PATENT NO.: 5,789,645
DATED: Aug. 4, 1998
INVENTOR(S): William L. Cox

It is certified that error appears in the above-identified patent and that said Letters Patent is hereby corrected as shown below:

| Col. | Line | |
|---|---|---|
| | | (Cover page) Insert --Related U.S. Application Data Continuation-in-part of Ser. No. 08/342,509, Nov. 21, 1994, patented.-- |
| 8 | 51 | reads "air feed is started to begin-partial oxidation of the aluminum trialkyl" should read --air feed is started to begin partial oxidation of the aluminum trialkyl-- |
| 10 | 24 | reads "A process of claim 5 further characterized" should read --A process of claim 6 further characterized-- |
| 11-12 | | Claims 21 and 22 are switched. |

Signed and Sealed this

Twenty-sixth Day of January, 1999

Attest:

Attesting Officer

*Acting Commissioner of Patents and Trademarks*